United States Patent [19]
Johnson et al.

[11] Patent Number: 6,039,721
[45] Date of Patent: Mar. 21, 2000

[54] METHOD AND CATHETER SYSTEM FOR DELIVERING MEDICATION WITH AN EVERTING BALLOON CATHETER

[75] Inventors: Kirk Johnson, Miami Lakes, Fla.; Merril L. Knudtson, Calgary, Canada

[73] Assignee: Cordis Corporation, Miami, Fla.

[21] Appl. No.: 08/984,576

[22] Filed: Dec. 3, 1997

Related U.S. Application Data

[62] Division of application No. 08/686,163, Jul. 24, 1996, abandoned.

[51] Int. Cl.⁷ .................................................. A61M 31/00
[52] U.S. Cl. ........................... 604/508; 604/500; 604/271; 604/96; 604/103
[58] Field of Search ..................... 604/271, 523, 604/103, 96, 101, 508, 509, 510, 500; 606/194, 192

[56] References Cited

U.S. PATENT DOCUMENTS

| | | |
|---|---|---|
| 3,911,927 | 10/1975 | Rich et al. . |
| 4,271,839 | 6/1981 | Fogarty et al. . |
| 4,479,497 | 10/1984 | Fogarty et al. . |
| 4,530,698 | 7/1985 | Goldstein et al. . |
| 4,606,347 | 8/1986 | Fogarty et al. . |
| 4,655,771 | 4/1987 | Wallsten . |
| 4,771,765 | 9/1988 | Choy et al. .............................. 600/18 |
| 4,820,270 | 4/1989 | Hardcastle et al. . |
| 4,848,343 | 7/1989 | Wallsten et al. ........................ 128/343 |
| 4,863,440 | 9/1989 | Chin . |
| 4,954,126 | 9/1990 | Wallsten . |
| 4,990,151 | 2/1991 | Wallsten . |
| 5,061,275 | 10/1991 | Wallsten et al. . |
| 5,074,845 | 12/1991 | Miraki et al. . |
| 5,163,927 | 11/1992 | Woker et al. . |
| 5,171,305 | 12/1992 | Schickling et al. . |
| 5,286,254 | 2/1994 | Shapland et al. ........................ 604/21 |
| 5,300,023 | 4/1994 | Lowery et al. . |
| 5,346,498 | 9/1994 | Greelis et al. . |
| 5,374,247 | 12/1994 | Lowery et al. . |
| 5,383,889 | 1/1995 | Warner et al. . |
| 5,389,089 | 2/1995 | Bauer et al. . |
| 5,458,573 | 10/1995 | Summers . |
| 5,514,093 | 5/1996 | Ellis et al. . |
| 5,549,551 | 8/1996 | Peacock, III et al. . |
| 5,630,797 | 5/1997 | Diedrich et al. . |

FOREIGN PATENT DOCUMENTS

| | | |
|---|---|---|
| 0 366 478 A2 | 5/1990 | European Pat. Off. . |
| 0 366 478 A3 | 5/1990 | European Pat. Off. . |
| 0 541 258 A1 | 5/1993 | European Pat. Off. . |

*Primary Examiner*—Corrine McDermott
*Assistant Examiner*—Cris Rodriguez
*Attorney, Agent, or Firm*—Michael W. Montgomery

[57] ABSTRACT

A balloon catheter having concentric, elongate lumen and guide tubes defining a lumen therebetween. An annular balloon has its proximal end secured to the lumen tube and its distal end secured to the guide tube. Relative axial movement of the tubes adjusts the balloon between retracted and extended positions. Processes for using the balloon catheter are also disclosed including performing angioplastic procedures on a plurality of stenoses of differing longitudinal extents during a single catheterization procedure, implanting self expanding stents in blood vessels treating occluded blood vessels and apply medications to diseased blood vessels.

2 Claims, 8 Drawing Sheets

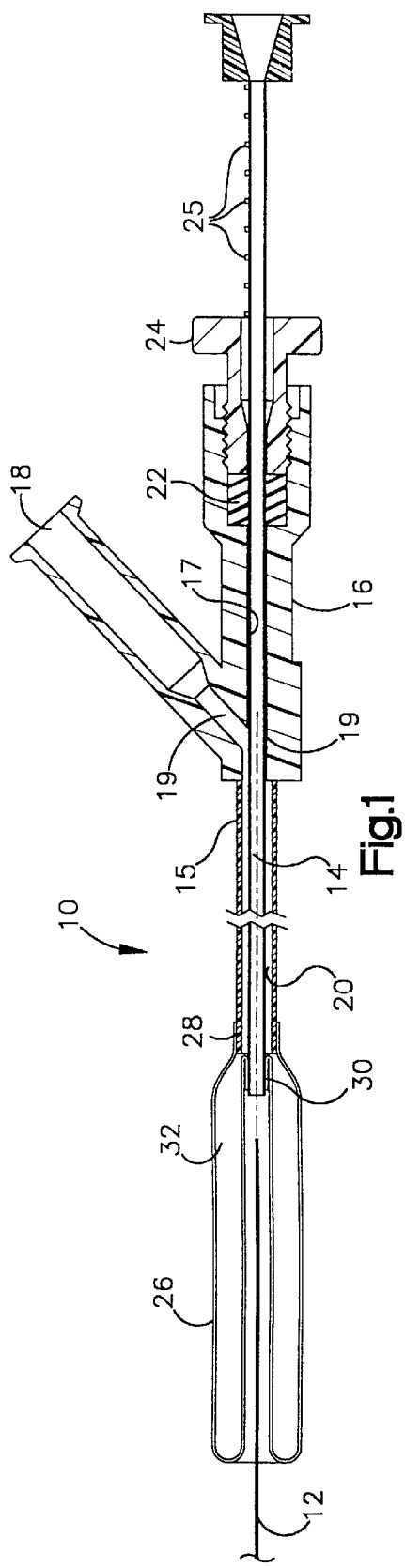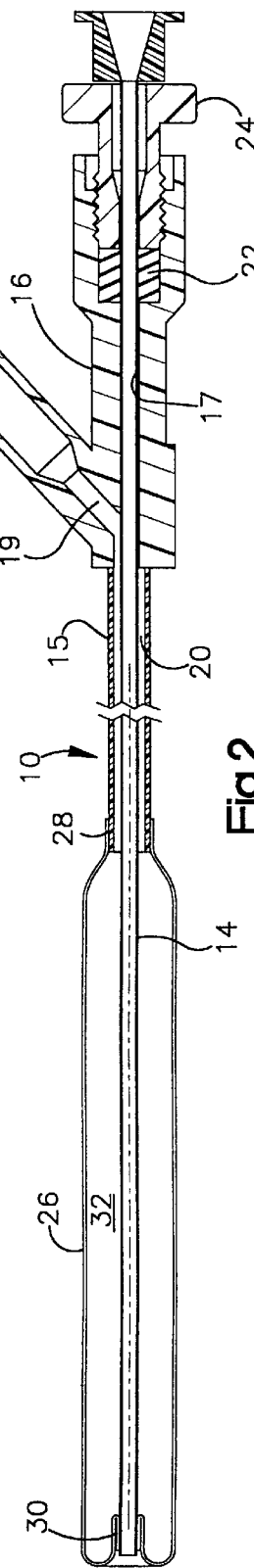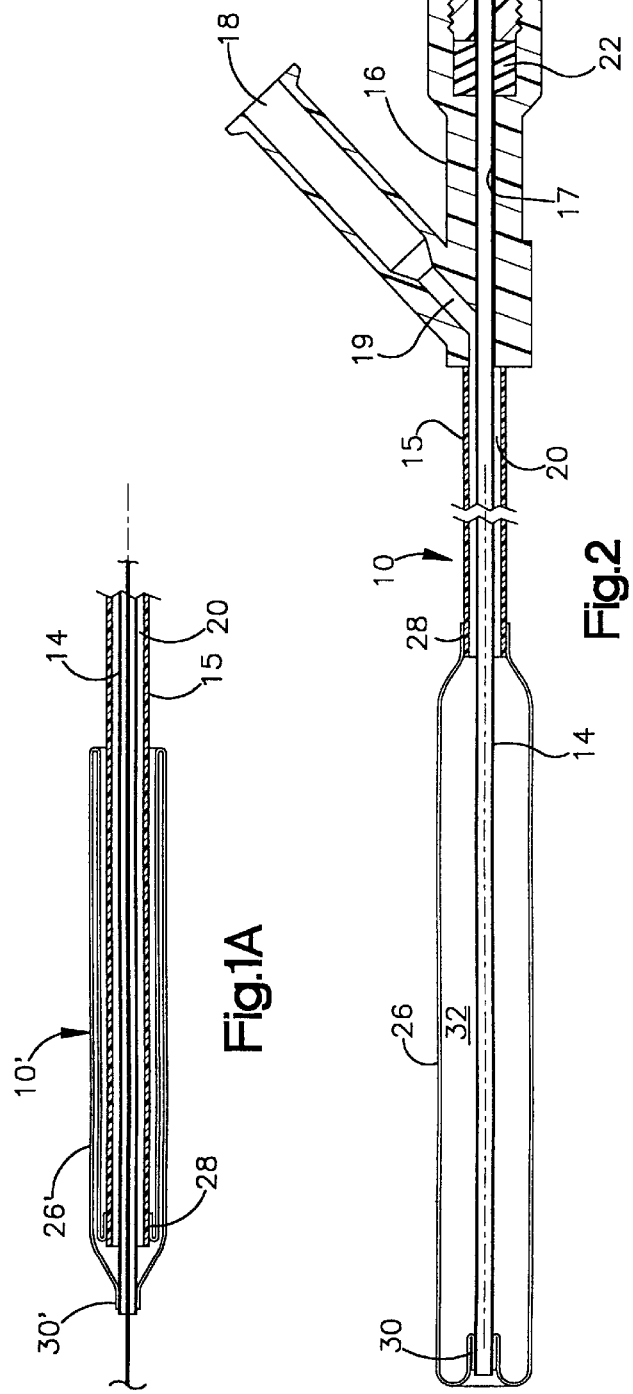

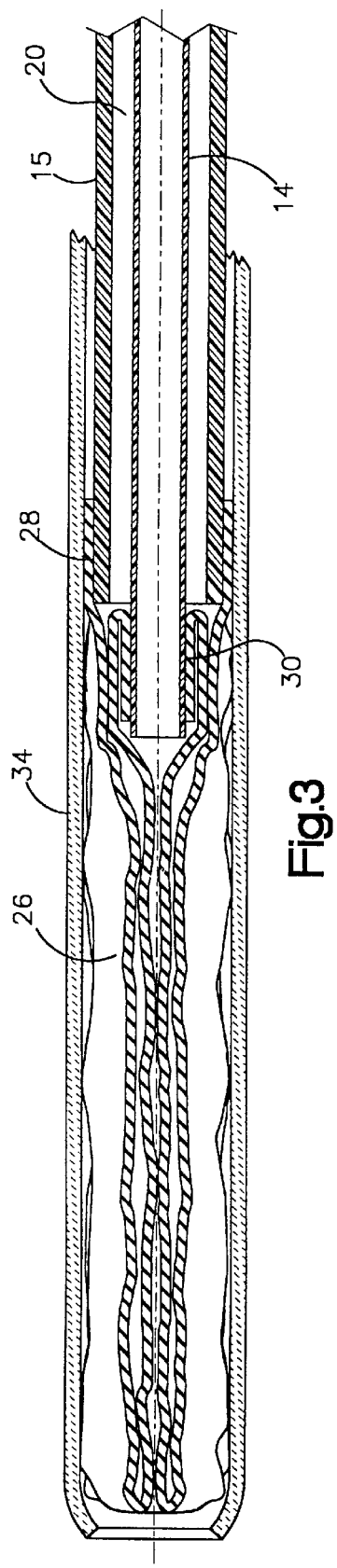
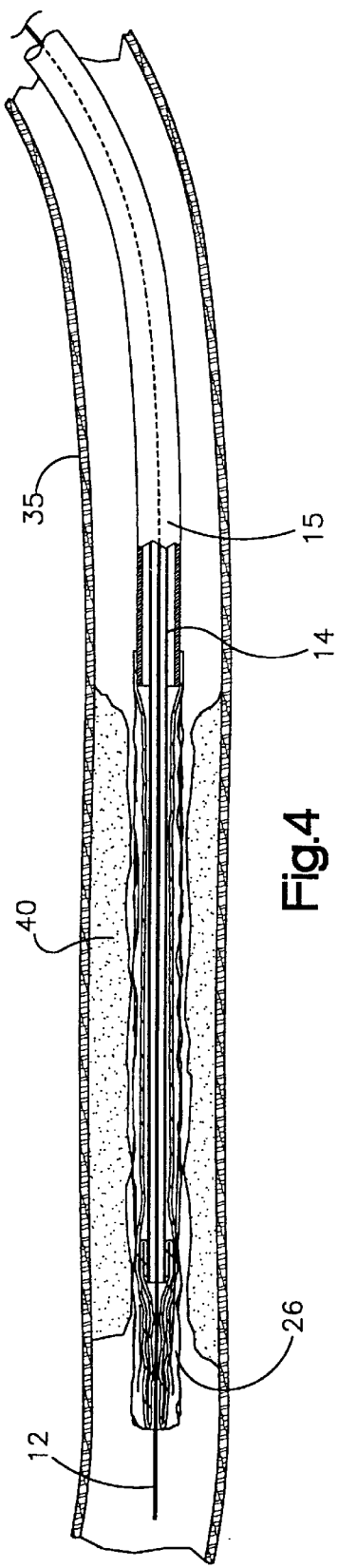
Fig.3
Fig.4

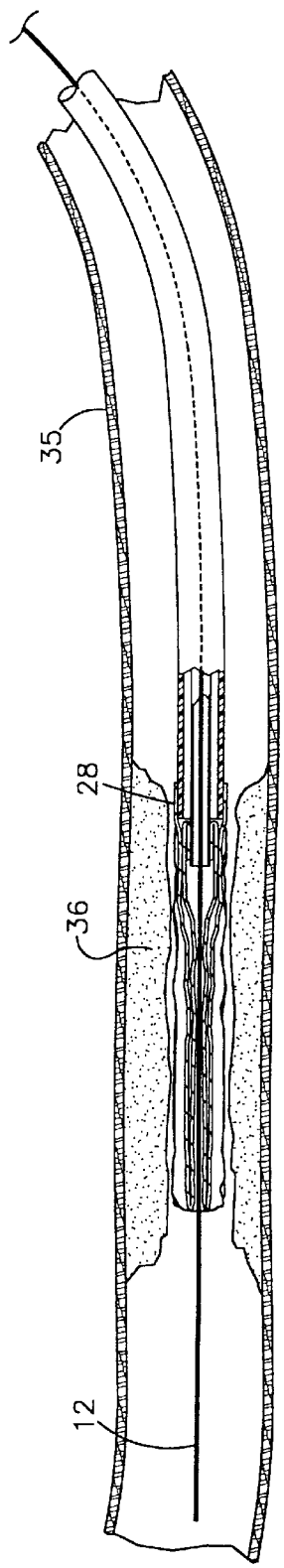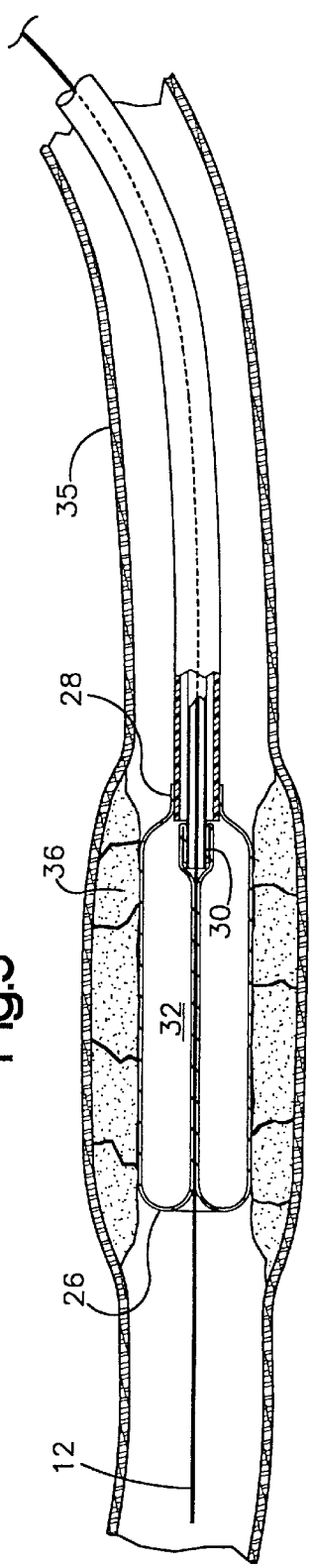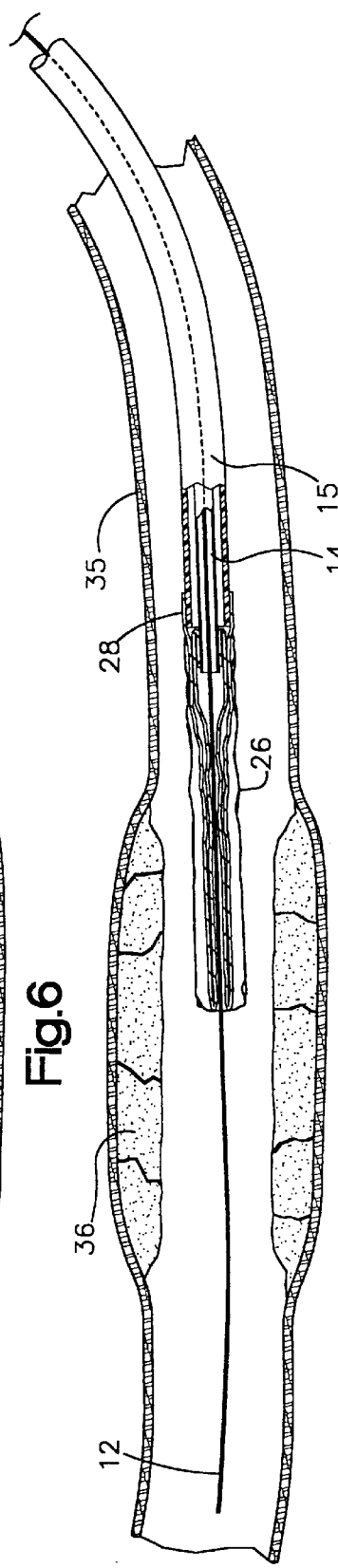

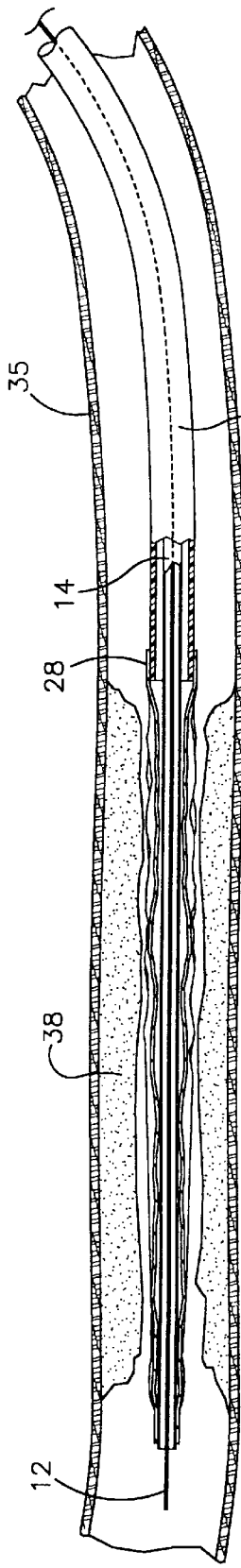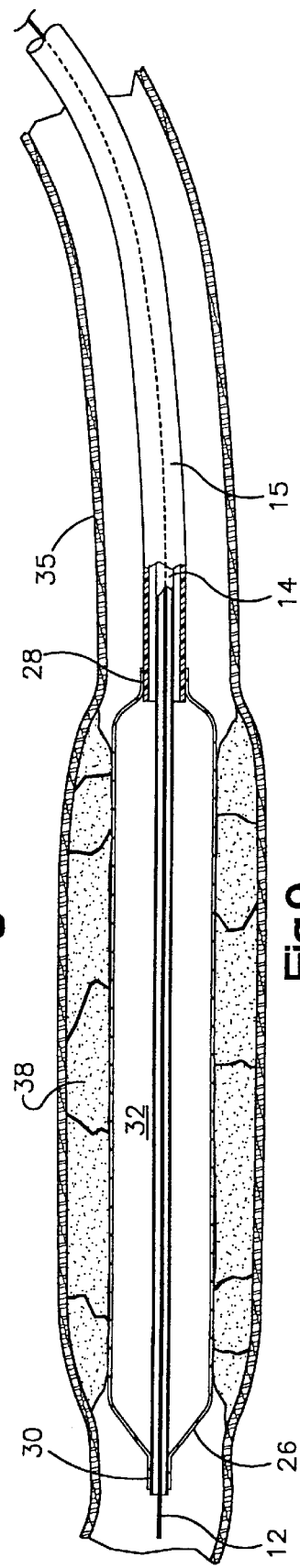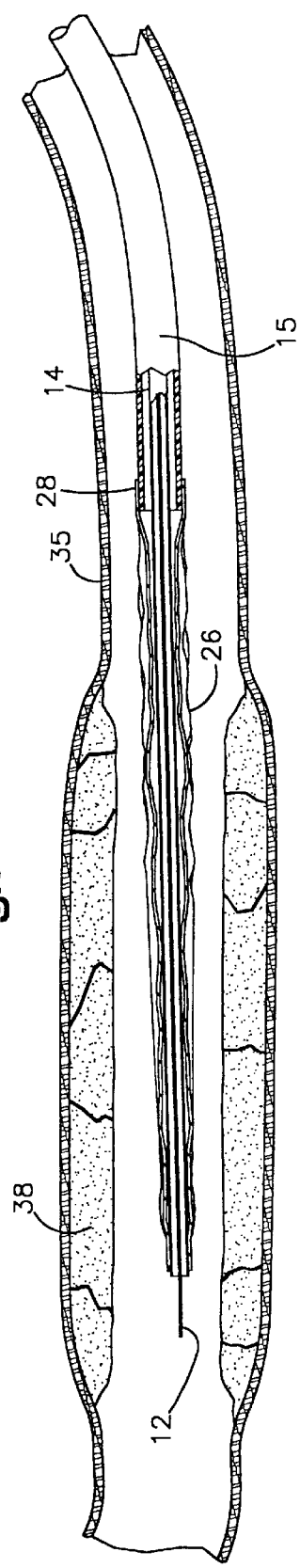

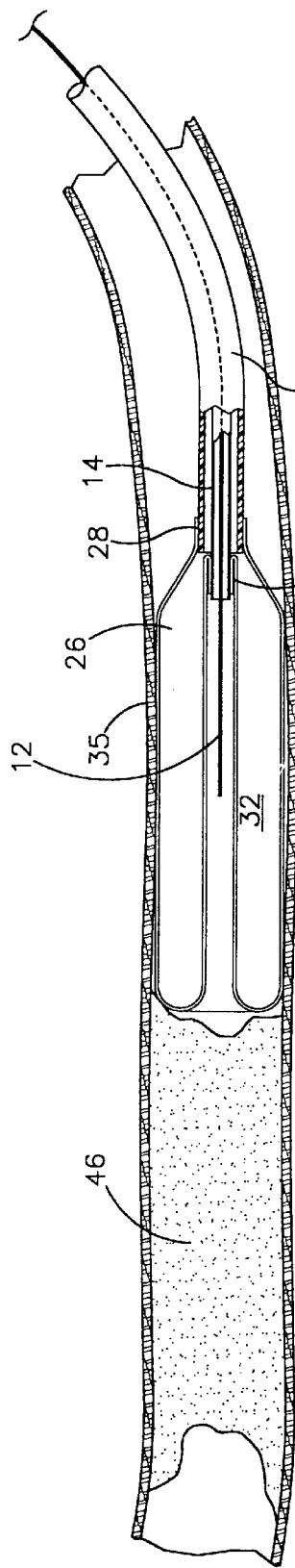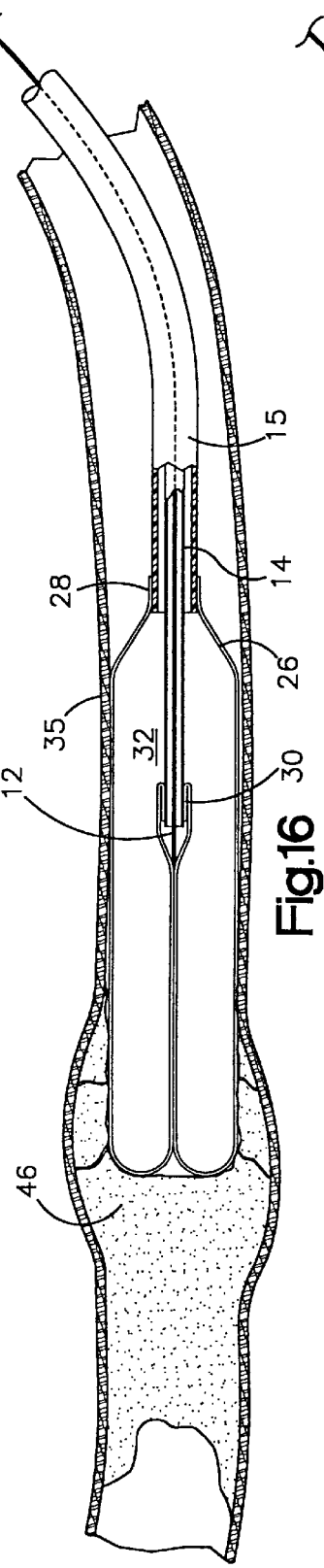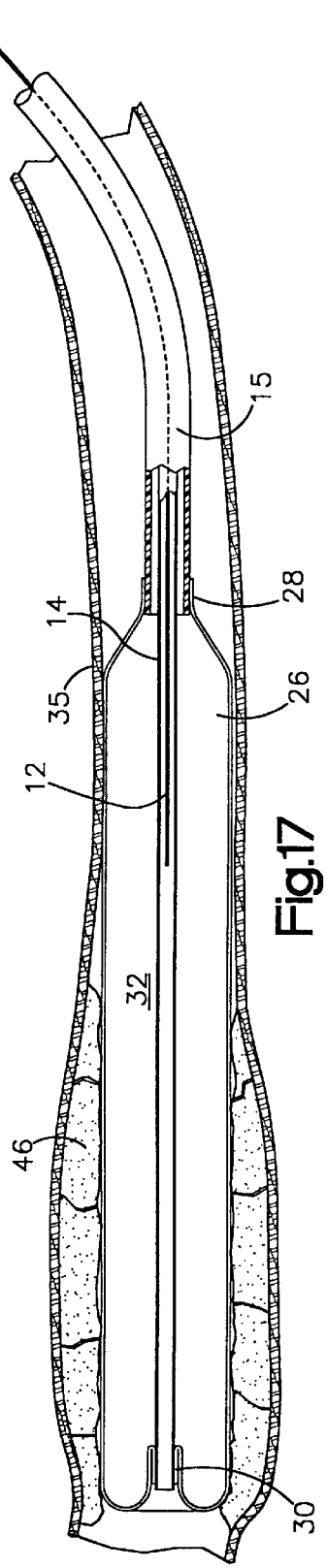

METHOD AND CATHETER SYSTEM FOR DELIVERING MEDICATION WITH AN EVERTING BALLOON CATHETER

"This is a divisional of Application Ser. No. 08/686,163, filed Jul. 24, 1996, now abandoned."

INTRODUCTION

This invention relates to catheters and more particularly to so called balloon catheters used in angioplasty.

BACKGROUND OF THE INVENTION

Angioplasty is a frequently used procedure for treating blockages in patients' blood vessels. With an angioplasty procedure, a balloon catheter is inserted into an obstructed blood vessel. An inflatable balloon, typically at the distal end of the catheter, is aligned with a stenosis effecting an obstruction in the vessel. Fluid is directed through an inflation lumen into the balloon to inflate the balloon and thereby extend the stenosis to provide an enlarged passage through it.

Prior to performing an angioplasty procedure, a physician will typically fluoroscopically examine the patient to locate a stenosis to be treated and determine its diameter and its length longitudinally of a blood vessel being obstructed by it. Balloon catheters are manufactured with balloons of a variety of sizes. A physician, having determined the axial length and diameter of a stenosis, will select a catheter of appropriate size and then perform the angioplasty procedure.

Where a patient has two or more stenoses, the lengths of the stenoses typically will be different. When such a condition is confronted, in the past it has been necessary for a physician to perform angioplasty with a catheter selected to be appropriate for one stenosis, remove that catheter from the patient following treatment of the one stenosis and then insert a second and different catheter to treat a second stenosis in order that catheters of appropriate size will be used for treatment of each stenosis. Such a procedure is time consuming and expensive due to the need for use of two catheters. In addition, there is a considerable increase in patient risk because of the time consumed and the complexity of the procedure. Clearly it would be desirable to be able to treat such conditions with a single insertion of one catheter.

Since balloons of prior catheters are made to fixed predetermined lengths, it is usually necessary to select a catheter of an axial length greater than a stenosis to be treated to assure expansion of the entire stenosis. As a consequence trauma is caused in adjacent less diseased regions. Accordingly, it would also be desirable to be able to adjust the effective length of a balloon to treat the stenosis while minimizing trauma in adjacent regions.

Where a total occlusion of an artery is present, success rates with angioplastic procedures have been very low. Where bridging collaterals or side branches to the occluded artery are present, an angioplastic guide wire tends to follow the path of least resistance, rather than to work its way through to the occlusion. Slightly higher success rates have been achieved with so called "olive" wires, that is guide wires each with an enlarged, somewhat olive shaped, distal end as described in an article by Meier et al. entitled "Magnum/Magnarail versus conventional systems for recanalization of chronic total coronary occlusions: a randomized comparison" published in the May 1992 issue of *American Heart*, pgs. 1182–6. Such guide wires have achieved somewhat better rates of success because an olive tends to prevent the wire from entering collaterals.

Prior procedures seeking to open occlusions with catheters have applied luminal forces to the atheromas. If excessive axial force is applied to an atheroma, it can create high shear forces at the atheroma-vessel interface. The shear forces tend to tear the atheroma lose from the arterial wall. Accordingly, it would be desirable to have angioplasty materials and procedures which would exert a more selective "digging" action in the center of an occluded vessel while preserving the integrity of the arterial wall.

When a self expanding stent is implanted in an artery, the stent is typically collapsed and then surrounded by an annular skin. Once the stent has been positioned within an artery at a location where it is to be implanted, the skin is pulled from around the stent as an axial force is applied to the stent to resist the pulling action. With such an arrangement, the initial force required to strip the surrounding skin is quite high because of the frictional resistance between the skin and the stent. Accordingly, this implantation procedure has limited the lengths of such expansible stents that can be implanted and suffered from other shortcomings as well.

With certain conditions it is desirable to administer drugs to vessel walls for treatment of an existing condition. Hydrogel coated balloons are utilized as delivery systems. Elaborate means are required to protect vessel surfaces from the coating as a coated balloon is deployed in a vessel to be treated. Clearly it would be desirable to have a simplified mechanism to protect vessel walls as a balloon coated with a medication is delivered to a location to be treated.

SUMMARY OF THE INVENTION

A catheter made in accordance with the present invention includes an elongate, tubular, inflatable balloon of annular cross section. The proximal end of the balloon is secured to the distal end of an inflation lumen tube with the balloon in fluid communication with a lumen delineated by the lumen tube. A guide wire tube is concentrically disposed within the lumen tube. The distal end of the guide wire tube is connected to the distal end of the balloon. The tubes and the connected balloon are relatively moveable axially to adjust the effective length of the balloon between contracted and extended positions.

Structure defining an inflation port is connected to the lumen tube. The structure has passages establishing fluid communication between the inflation port and the lumen. An adjustable seal is interposed between the structure and the guide wire tube. When tightened, the seal secures the guide wire tube in a selected position relative to the lumen. In that the guide wire tube and lumen tube are in fixed relative positions, the respectively connected distal and proximal ends of the balloon are also in fixed relationship, at least longitudinally. When the seal is adjusted to a release position, the guide tube and the lumen tube may be moved axially relatively to adjust the effective length of the balloon between its retracted and extended positions. Indicia on the guide wire tube indicate to the user the relative spacing of the balloon distal and proximal end attachment points.

Two embodiments are disclosed. In both embodiments the proximal and distal ends of the balloon are adjacent one another with the balloon folded back on itself when positioned for minimal effective length. In one embodiment the balloon extends rearwardly from the distal ends of the tubes in a position surrounding the tubes. In the other embodiment the balloon extends outwardly or forwardly from the tube distal ends.

In order to condition an adjustable length balloon for insertion into a patient's blood vessel, the balloon is compressed into a conventional sterilization tube. The balloon is then sterilized with known and conventional sterilization processes. Since the balloons are formed of thermo plastic materials, such as nylon or PET, heat of sterilization temporarily fixes walls of the balloon in its short effective length and compressed condition, enabling insertion of a balloon into a patient while the balloon is in such condition with either embodiment.

When a plurality of stenoses are to be treated with a single catheter insertion, the balloon will preferably be positioned within the stenosis to be treated having the shortest length longitudinally of a blood vessel and the balloon will be inflated. Once that stenosis has been treated, the balloon is deflated, and the catheter is moved into registration with another stenosis. The effective length of the balloon is adjusted to a length appropriate for treatment of the second stenosis by relatively shifting the tubes and thereafter the balloon is again inflated. Upon deflation, the balloon may be moved to yet another stenosis to be treated. If there are more than two stenoses to be treated in a single catheterization of a patient, it is preferable that they be treated sequentially from the shortest to the next shortest and so forth to the longest stenosis as measured longitudinally of the vessel or vessels being treated.

Where a total occlusion is to be treated, an expansible annular balloon is inserted in its retracted condition until the balloon abuts the occlusion. Thereafter the balloon is inflated and expanded as the guide tube is slowly advanced. This procedure allows the balloon to exert a "digging" force against the occlusion. With such a procedure the balloon is intended to burrow through the atheroma gradually, radially expanding the atheroma as it works its way along the vessel to open the occluded artery.

In another application of the balloon catheter of this invention, a self expanding stent is collapsed. The balloon is positioned around the stent with the lumen tube advanced and positioned close to the end of the guide tube. According to the procedure being followed, the balloon is preferably deflated, folded on itself and surrounding the stent.

Where the stent is surrounded by a deflated balloon, the balloon is advanced into the vessel to be treated until it is within a stenosis to be treated. The lumen tube is then held stationary while the guide tube is advanced to peel the balloon from the stent. Thus, the balloon will be peeled gradually from the stent working from the proximal to the distal end of the stent and allowing the stent to expand and thereby become implanted at a desired location. Thereafter the catheter is preferably withdrawn a short distance to position the balloon within the stent, the balloon is inflated to assure full stent expansion and then the catheter is removed from the vessel being treated When a medication is to be applied to a diseased section of a blood vessel wall, the balloon embodiment which is folded on itself rearwardly and disposed around the lumen tube is utilized. A portion of the balloon surface which is adjacent the lumen tube carries the medication to be applied while the remainder of the balloon external surface external of the tube is free of medication. The catheter is then inserted into the vessel to be treated and advanced until the balloon has passed through the diseased section. The balloon is then inflated to bring the external balloon surface into engagement with the vessel wall adjacent the diseased section and thereby anchor the catheter in a position longitudinally of the vessel. The guide tube is then held in fixed location longitudinally as the lumen tube is withdrawn and balloon inflation continues to bring the medicated portion of the balloon surface into engagement with the diseased section and thereby apply the medication to the section.

Accordingly, the objects of the invention are to provide a novel and improved balloon catheter having a balloon of adjustable effective length and processes of utilizing such a catheter for expanding stenoses, opening occlusions, protecting and implanting stents and applying medications to diseased vessel wall segments.

DESCRIPTION OF THE DRAWINGS

FIG. 1 is a foreshortened sectional view of the balloon catheter of this invention with the components positioned to show the balloon in a position of intermediate length;

FIG. 1a is a foreshortened sectional view of an alternate embodiment of the catheter of this invention;

FIG. 2 is a view corresponding to FIG. 1 showing the balloon in its maximum length position and inflated;

FIG. 3 is a sectional view of the balloon in its position of minimal length and inserted in a sterilization tube to undergo sterilization procedures;

FIG. 4 shows the balloon in a partially extended, but deflated, condition within a stenosis of intermediate length;

FIG. 5 shows the balloon in a retracted and deflated condition positioned within a stenosis of relatively short length longitudinally of the blood vessel being treated;

FIG. 6 corresponds to FIG. 5, but with the balloon expanded to show the angioplastic procedure on the stenosis of FIGS. 5 and 6;

FIG. 7 shows the balloon in a collapsed condition being removed from the stenosis of FIGS. 5 and 6;

FIGS. 8–10 illustrate treatment of a relatively long stenosis with the balloon in an extended and collapsed condition in FIG. 8, in an inflated condition expanding the stenosis in FIG. 9; and a collapsed condition to be removed from the stenosis in FIG. 10;

FIG. 15 illustrates the catheter positioned to open up an occluded blood vessel;

FIG. 16 illustrates the balloon of the catheter of this invention advancing through an atheroma of an occluded vessel;

FIG. 17 illustrates the conclusion of the occlusion relieving process of FIGS. 13–15, with the balloon having advanced fully through the atheroma and being ready for deflation and withdrawal;

DETAILED DESCRIPTION

Figure 11:
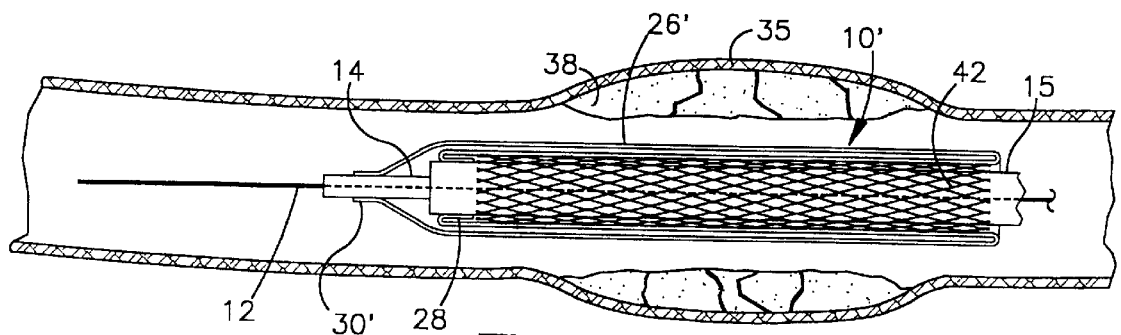
FIGS. 11–14 are sequential views of implantation of a self expanding stent utilizing the catheter of the alternate embodiment of this invention.

Referring to the drawings and to FIGS. 1 and 2 in particular, one embodiment of a catheter is shown generally at 10. The catheter 10 utilizes the usual guide wire 12. An elongate tubular guide tube 14 surrounds the guide wire. In use the guide tube 14 is slidable longitudinally of the guide wire for insertion into and withdrawal from a blood vessel of a patient being treated.

An elongate cylindrically contoured lumen tube 15 is concentrically disposed about the guide tube 14. A catheter control structure 16 has an elongate through guide tube receiving passage 17. The control structure is fixed to the proximal end of the lumen tube 15.

The control structure 16 also includes an inflation/deflation port 18 communicating through passage 19 with a lumen 20. The lumen 20 is an annular passage with its perimeter delineated by the lumen tube 15 and its inner circumference by the guide tube 14.

The control structure carries an annular seal 22 which circumscribes the guide tube 14. An annular thumb screw 24 is threaded into the control structure 16 for controllably compressing the seal 22 to effect a fluid tight seal between the structure and the guide tube 14.

The guide tube 14 has a plurality of position indicating indicia 25 near its proximal end. The indicia 25 function to indicate to an operator relative longitudinal spacing of the distal ends of the guide and lumen tubes 14, 15.

An annular angioplasty balloon 26 is provided. The balloon 26 has a proximal end connected to the distal end of the lumen tube at 28. The distal end of the balloon 26 is connected to the distal end of the guide tube 14 at 30.

As indicated by a comparison of FIGS. 1 and 2, the guide tube is relatively moveable, when the seal 22 is released, between a retracted position as shown in FIG. 1 and an extended position as shown in FIG. 2. Thus, the balloon is adjustable between the position of FIG. 1 where the balloon is folded on itself and the position of FIG. 2 where the balloon 26 is fully extended. The effect of this adjustment is to vary an inflation/deflation volume 32 which is essentially fully defined by the balloon 26 in the retracted position of FIG. 1. The inflation space 32 is perimetrically defined by the balloon 26 with its inner circumference defined by the guide tube 14 when the guide tube and balloon are in their fully extended positions as shown in FIG. 2.

FIG. 1a is a foreshortened, sectional view of an alternate embodiment of the catheter 10'. Modified parts as contrasted with the embodiment of FIGS. 1 and 2, are identified by like reference numerals with a "'" added, while identical parts carry the same reference numerals. As will be seen by an examination of FIG. 1a, the balloon 26' rather than being folded on itself in a direction forwardly of the catheter when in its shortened position, is folded on itself rearwardly to surround and overlie the lumen tube 15. To this end the connection 30' of the distal end of the balloon 26' and the guide tube 14', is not folded on itself as it is in the embodiments of FIGS. 1 and 2.

Preparation for Use

When the catheter 10 or 10' is to be used to treat a patient, the thumb screw 24 is loosened and the guide tube 14 is retracted relative to the lumen tube 15 and the control structure 16 or the lumen tube and the structure are advanced relative to the guide tube to position the balloon in its retracted position of FIG. 1 or FIG. 1a and in a deflated condition. The balloon is then inserted into a sterilization tube 34 as shown in FIG. 3. The catheter is then subjected to the usual sterilization procedures utilizing ethelene oxide gas at elevated temperatures. The effect of the sterilization procedures is that the thermoplastic material of which the balloon 26 is composed is temporarily set in its compressed and deflated condition through the heat of sterilization. In practice angioplasty balloons are made of a variety of thermoplastic materials, including nylon, PET and polyethylene. For the present disclosure nylon is the preferred material.

Angioplasty Procedures

One of the outstanding advantages of the present invention is that in effect one has a single catheter to accomplish what previously took a set of catheters of a range of sizes. With the catheter of this invention, a plurality of stenoses may be treated with a single catheterization.

Turning first to FIGS. 5, 6 and 7, a guide wire 12 is inserted into a blood vessel 35. The guide and lumen tubes are then advanced as a unit by pushing the control structure 16 toward the patient. The advance along the guide wire is continued until the balloon 26 in its collapsed and retracted position is within an atheroma 36 of relatively short length longitudinally of the vessel 35 as depicted in FIG. 5. Fluid under pressure is then directed through the port 18. The fluid is communicated through the lumen 20 into the space 32 within the balloon 26 until the balloon achieves the inflated condition of FIG. 6. The balloon distends the plaque of the atheroma 36 and the wall of the vessel 35 to relieve the stenosis.

Once the angioplasty procedure to distend the atheroma 36 has been completed, the balloon is deflated and the catheter 10 is moved, FIG. 7. At this juncture if there is a second stenosis to be treated, the balloon is moved to a second and longer atheroma 38, FIG. 8. At a time which might either proceed or follow the positioning relative to the second atheroma 38, the thumb screw 24 is loosened to relax the seal 22. The guide tube 14 is then shifted axially relative to the lumen tube 15 and the control structure 16 to adjust the balloon to an appropriate length. As shown in FIGS. 8 and 9, the adjustment has been to substantially the fully extended length of the balloon.

Once the length adjustment has been completed, the thumb screw 24 is tightened to compress the seal and fix the tubes 14, 15 in their newly adjusted relative positions. Once this adjustment has been completed and the balloon 26 is appropriately located within the atheroma 38, the balloon is again inflated, this time to distend the atheroma 38 and the vessel 35 to the condition indicated in FIG. 9. When the angioplastic plaque expansion procedure has been completed, the balloon is again deflated. If there are further stenoses in the same blood vessel 35 to be treated, the length adjustment and repositioning procedure will be repeated. If there are no further stenoses to treat, the catheter is withdrawn from the vessel 35.

Where a stenosis of intermediate length as shown at 40 in FIG. 4 is present, the balloon length will be adjusted to an intermediate length as indicated in FIG. 4. Preferably the sequence of stenosis treatment when there are three or more is to, referring to the illustrations, treat the short stenosis 36 of FIGS. 5 to 7, the intermediate stenosis 40 of FIG. 4, and thereafter the longest stenosis 38 of FIGS. 8 to 10.

Stent Implantation

Where the potential for re-occlusion and restenosis is relatively high, it has become accepted practice to insert a stent into a section of the blood vessel that has been expanded through an angioplastic procedure. Self expanding stents are useful for certain clinical indications. The balloon catheter of this invention is highly suitable for implanting such stents with the catheter of the alternate embodiment being preferred when the vessel to be treated is of sufficient diameter .

Referring now to FIGS. 11 to 14, a self expanding stent 42 is shown in a compressed condition in FIG. 11. For illustrative purposes FIGS. 11 to 14 show the stent being positioned within the expanded long stenosis 38 of FIGS. 8 through 10.

Prior to insertion of the catheter 10 to implant the stent 42, the stent is telescoped over the lumen tube 15. The catheter is adjusted to position the balloon in its retracted position of FIG. 1a. The stent is compressed to a diameter small enough to position it within the balloon 26' and adjacent the distal end of the lumen tube 15. When so positioned the balloon functions to constrain the stent 42 in its compressed condition. Preferably the balloon is fully deflated to the point where the balloon is longitudinally folded on its self to provide inner and outer contacting layers circumscribing and constraining the stent.

Figure 12:
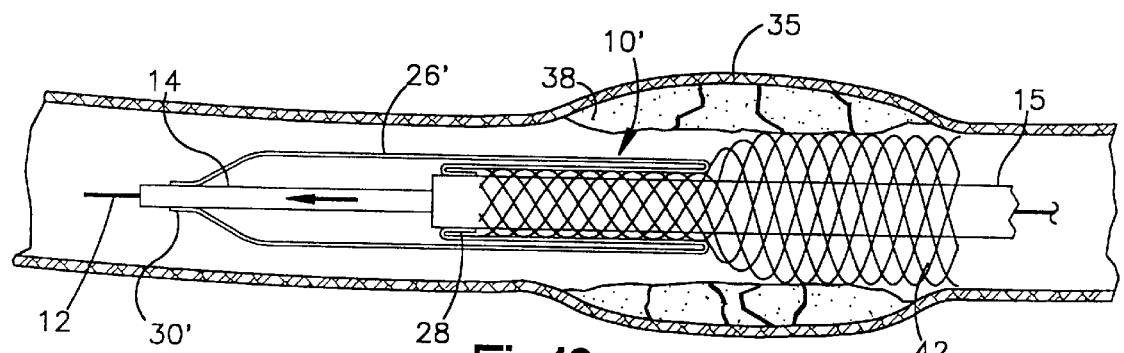
Figure 13:
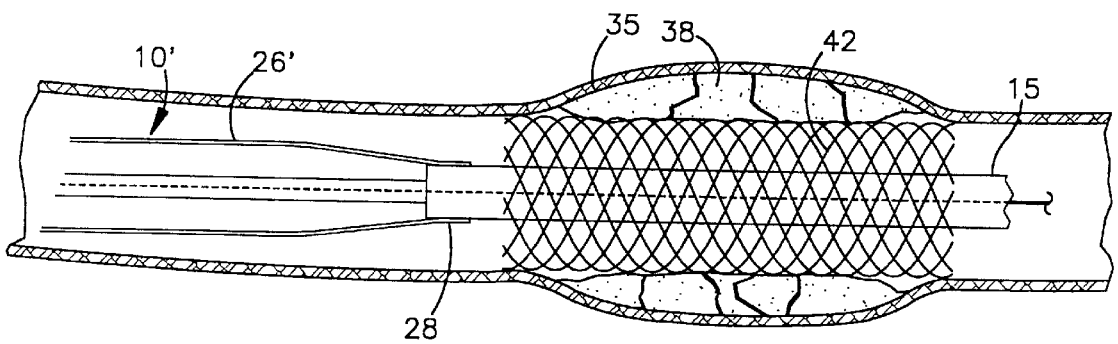
Figure 14:
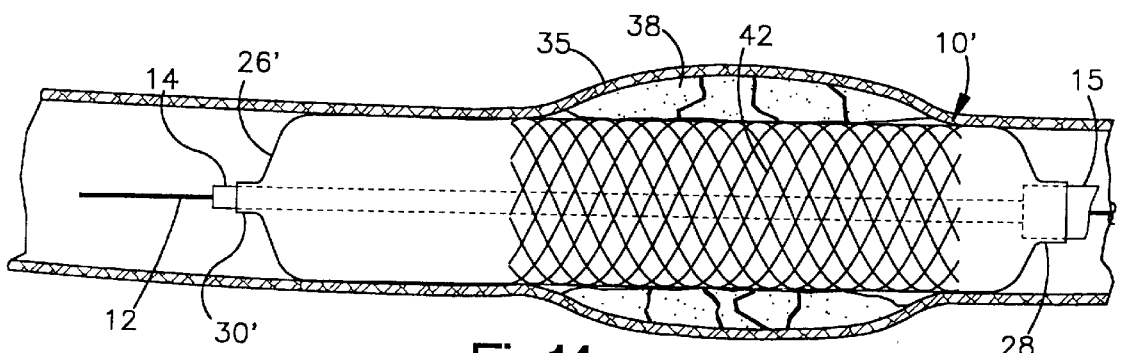

After the stent has been compressed and positioned within the balloon, the catheter is inserted until the stent is located within the expanded atheroma 36. Once the balloon is appropriately positioned, the seal 22 is relaxed to the extent necessary to permit relative axial movement of the tubes 14, 15 as illustrated in FIGS. 12 and 13. The lumen tube is then held stationary as the guide tube is advanced. The advance of the guide tube 14 is continued to literally peel the balloon from the stent, allowing it to expand to the position of FIG. 13. Where some return or restenosis has been experienced, the balloon may be positioned within the stent and inflated to return the plaque of the stenosis 36 to its expanded condition, as illustrated in FIG. 14. Thereafter the catheter is withdrawn.

Figure 22:
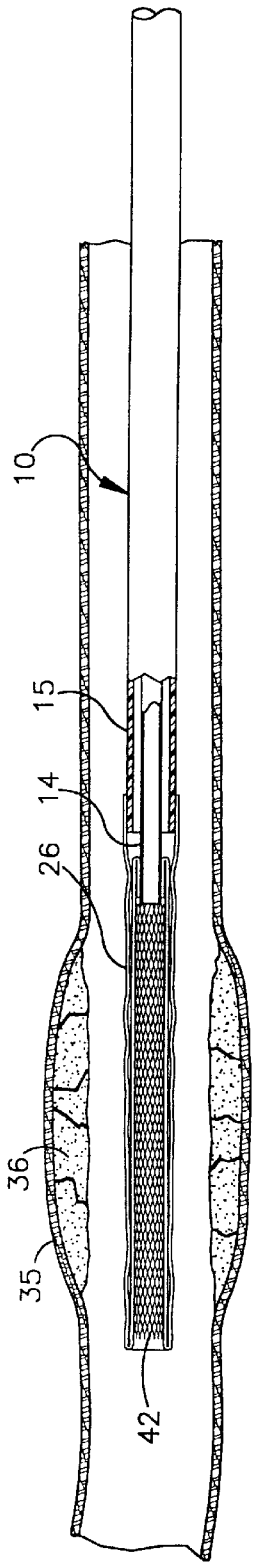
Figure 23:
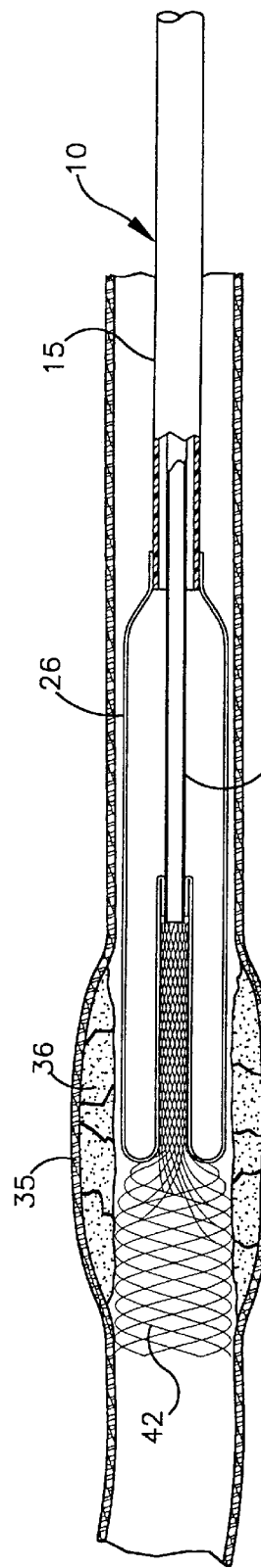
Figure 24:
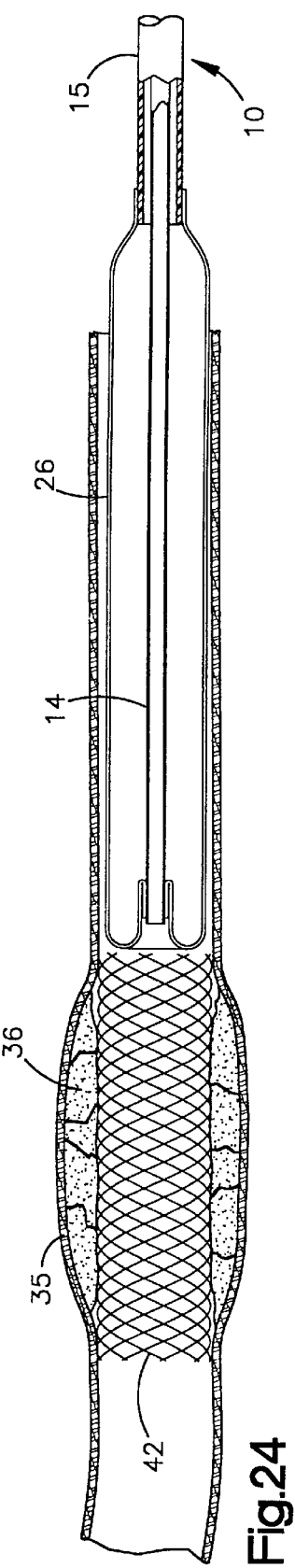

When the stent implantation process dictates a smaller profile than the arrangement of FIGS. 11–14, the arrangement depicted in FIGS. 22–24 is used. Referring now to FIGS. 22–24, a self expanding stent 42 is shown in a compressed condition in FIG. 22. For illustrative purposes FIGS. 22–24 show the stent being positioned within the expanded small stenosis 36 of FIGS. 5 through 7.

Prior to insertion of the catheter 10 to implant the stent 42, the stent is telescoped over the lumen tube 15. The catheter is adjusted to position the balloon in its retracted position of FIG. 1. The stent is compressed to a diameter small enough to position it within the balloon 26 and against the distal end of the guide tube 14. When so positioned the balloon functions to constrain the stent 42 in its compressed condition. Preferably the balloon is fully deflated to the point where the balloon is longitudinally folded on its self to provide inner and outer contacting layers circumscribing and constraining the stent.

After the stent has been compressed and positioned within the balloon, the catheter is inserted until the stent is located within the expanded atheroma 36. Once the balloon is appropriately positioned, the seal 22 is relaxed to the extent necessary to permit relative axial movement of the tubes 14, 15 as illustrated in FIGS. 23 and 24. The lumen tube is then retracted as the guide tube is maintained stationary and engagement with the stent 42 to resist retractive motion of the stent. The retraction of the lumen tube 15 is continued to literally peel the balloon from the stent, allowing it to expand to the position of FIG. 24. Where some return or restenosis has been experienced, the balloon may be positioned within the stent and inflated to return the plaque of the stenosis 36 to its expanded condition, as illustrated in FIG. 14. Thereafter the catheter is withdrawn.

Occluded Vessel Treatment

Referring to FIGS. 15–17, a process for relieving an obstruction in an occluded vessel is shown. The catheter is advanced along the guide wire 12 until the balloon 26 is positioned adjacent an atheroma 46 to be treated. At this juncture the guide tube 14 is in its fully retracted condition such that the balloon distal end connection 30 is immediately adjacent the proximal end connection 26.

As the balloon is inflated it expands against vessel walls adjacent the occlusion and in so doing anchors the balloon against retraction as the balloon is further inflated. As inflation continues the guide tube 14 is advanced slowly either manually or by overcoming friction between the seal 22 and the guide tube with the fluid pressure in the balloon. As the inflation and advance occur, the balloon works its way axially through the atheroma 46, as illustrated in FIG. 16, until the balloon has worked its way fully through the atheroma 46 as illustrated in FIG. 17. After the balloon has advanced through the atheroma the balloon is deflated and the catheter is withdrawn leaving the occlusion opened such that blood flow through the vessel 35 is restored.

Alternately where conditions permit, an alternate a first step in the process a guide wire 12' is fed through the vessel. The guide wire 12' is preferably of the type which has an enlarged tip 45, known as an "olive" due to its shape having a physical resemblance to an olive fruit.

Local Drug Delivery

Figure 18:
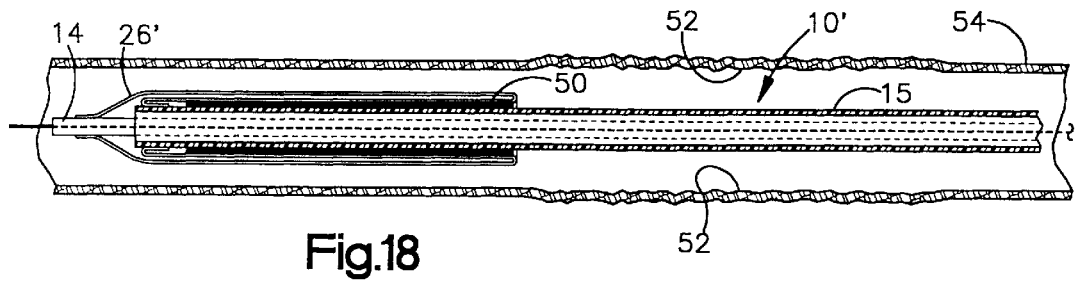
FIGS. 18–21 are sequential views of the catheter of the alternate embodiment of this invention utilized for drug delivery to a diseased section of a blood vessel; and, FIGS. 22–24 illustrate an alternate stent implantation.

Referring now to FIGS. 18–21, a local drug delivery system is illustrated. With this procedure the alternate embodiment of FIG. 1a is utilized. A medication carried by a hydrogel or other carrier 50 is applied to that section of the external surface of the balloon 26' which is adjacent and surrounding the lumen tube 15 when the balloon 26' is in its collapsed and foreshortened position as shown in FIG. 18. Thus, the external surface of the balloon when it is in the condition illustrated in FIG. 18, is free of the medication in order that the medication will not be inadvertently administered other than to the specific diseased region to be treated. This diseased region is illustrated at 52 in FIGS. 18–21.

Figure 19:
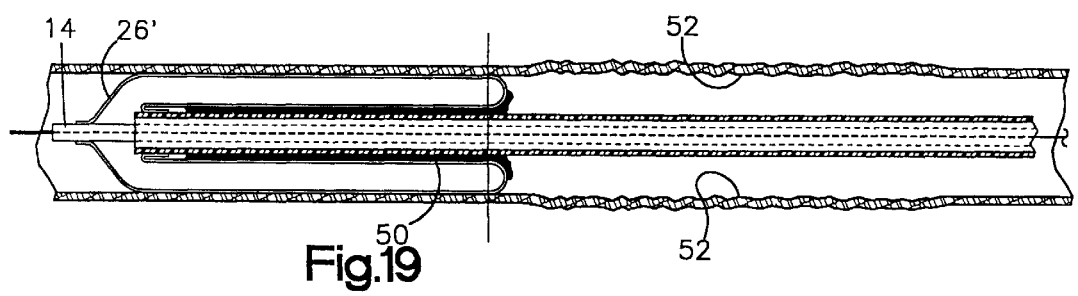
Figure 20:
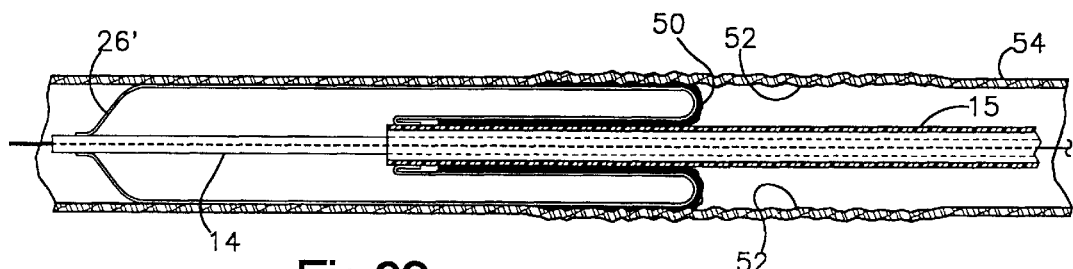
Figure 21:
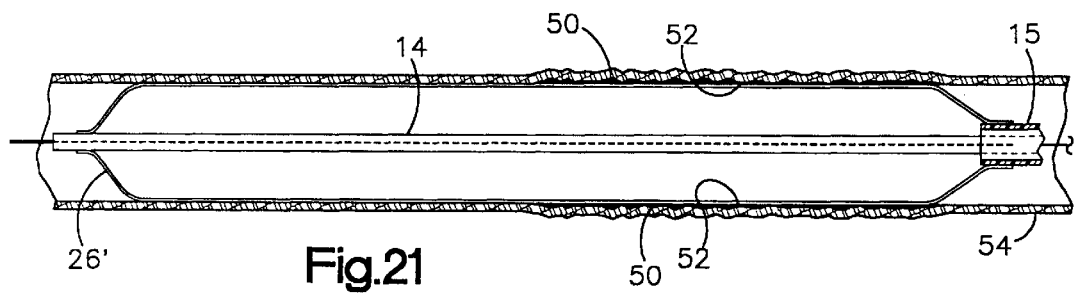

In the drug delivery process the catheter 10' with the balloon 26' in its collapsed condition of FIG. 18, is inserted into a blood vessel 54 to be treated. The insertion is continued until the balloon has passed through the diseased region 52. The guide tube 14 is restrained in the location depicted in FIG. 18. The balloon is then partially expanded as illustrated in FIG. 19 to anchor the catheter 10' in its position with the balloon immediately past the diseased region 52.

As a next step, the lumen 15 is retracted, while the guide tube 14 is maintained longitudinally fixed in the blood vessel 54. As the lumen tube 15 is withdrawn the balloon inflation is continued as the guide tube withdrawal continues, FIG. 20, until the balloon is in its fully extended and inflated condition of FIG. 21 to apply the drug to, but essentially only to, the diseased region 52. Thereafter the balloon is deflated and the catheter is withdrawn from the vessel 54.

Although the invention has been described in its preferred form with a certain degree of particularity, it is understood that the present disclosure of the preferred form has been made only by way of example and that numerous changes in the details of construction, operation and the combination and arrangement of parts may be resorted to without departing from the spirit and the scope of the invention as hereinafter claimed.

We claim:

1. A process of applying a medication to a diseased portion of a blood vessel with a catheter having a balloon connected to distal ends of inner and outer tubes, comprising:

providing a balloon catheter having an inner and outer tube which are longitudinally adjustable with respect to each other, and a balloon affixed at opposing ends of the balloon to a distal end of one of the inner and outer tubes; the balloon defining a medication portion, and a lumen being defined between the inner and outer tubes;

applying a coating of medication to the medication portion of a surface of the balloon;

positioning distal ends of the inner and outer tubes in closely spaced relationship and folding the balloon on itself such that the balloon assumes an annular everted shape defining inner and outer balloon layers, wherein the entire balloon surrounds some portion of one of the inner and outer tubes; the medication portion of the balloon being arranged on the inner layer which is internal, and the balloon having a shielding portion of the balloon on the outer layer which surrounds the remainder of the balloon;

inserting the catheter into the vessel and positioning the balloon adjacent the diseased portion of the blood vessel;

inflating the balloon by delivering fluid through the lumen defined between the tubes and communicating with the balloon;

continuing the inflation until the shielding portion engages the vessel adjacent the diseased portion;

longitudinally adjusting the inner and outer tubes relatively to unfold the balloon as the inflation continues, thereby bringing the medication portion into contact with the diseased portion of the blood vessel, to apply the medication to the diseased portion; and deflating the balloon and removing the catheter from the vessel.

2. A process of applying a medication to a diseased portion of a blood vessel with a catheter having a balloon connected to distal ends of inner and outer tubes, comprising:

providing a balloon catheter having an inner and outer tube which are longitudinally adjustable with respect to each other, and a balloon affixed at opposing ends of the balloon to a distal end of one of the inner and outer tubes; a lumen being defined between the inner and outer tubes;

positioning the distal ends of the inner and outer tubes in closely spaced relationship with the balloon folded on itself to form an annular everted shape defining inner and outer folds, the balloon defining a medication portion on the inner fold having a medication coating the inner fold surface while a shielding portion on the outer fold of the balloon surrounds the remainder of the balloon, wherein the entire balloon surrounds some portion of one of the inner and outer tubes;

inserting the catheter into the vessel and positioning the balloon adjacent the diseased portion;

inflating the balloon by delivering fluid through a lumen defined between the tubes and communicating with the balloon;

continuing the inflation until the shielding portion engages the vessel adjacent the diseased portion;

longitudinally adjusting the inner and outer tubes relatively to unfold the balloon as the inflation continues, thereby bringing the medication portion into contact with the diseased portion to apply the medication to the diseased portion; and deflating the balloon and removing the catheter from the vessel.

* * * * *